United States Patent
Paul

(10) Patent No.: US 8,475,502 B2
(45) Date of Patent: Jul. 2, 2013

(54) LOAD DISTRIBUTION CROWN

(75) Inventor: David C. Paul, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 101 days.

(21) Appl. No.: 12/572,980

(22) Filed: Jan. 12, 2010

(65) Prior Publication Data
US 2010/0106201 A1    Apr. 29, 2010

Related U.S. Application Data

(62) Division of application No. 10/819,934, filed on Apr. 8, 2004, now Pat. No. 7,615,069.

(51) Int. Cl.
*A61B 17/70*     (2006.01)

(52) U.S. Cl.
USPC ............................ 606/272; 606/319; 606/290

(58) Field of Classification Search
USPC .................. 606/63–73, 86 A, 280, 287–288, 606/291, 297, 305, 267–270, 272, 289, 290, 606/301, 319, 328
See application file for complete search history.

(56) References Cited

U.S. PATENT DOCUMENTS

| | | | | |
|---|---|---|---|---|
| 3,680,619 A | * | 8/1972 | Sparks | 411/134 |
| 4,988,351 A | * | 1/1991 | Paulos et al. | 606/232 |
| 5,269,784 A | * | 12/1993 | Mast | 606/288 |
| D368,777 S | * | 4/1996 | Goble et al. | D24/146 |
| 5,725,541 A | * | 3/1998 | Anspach et al. | 606/151 |
| 5,976,141 A | * | 11/1999 | Haag et al. | 606/292 |
| 6,228,087 B1 | * | 5/2001 | Fenaroli et al. | 606/324 |
| 6,565,567 B1 | * | 5/2003 | Haider | 606/266 |
| 6,569,186 B1 | * | 5/2003 | Winters et al. | 606/232 |

\* cited by examiner

*Primary Examiner* — David Isabella
*Assistant Examiner* — Suba Ganesan

(57) ABSTRACT

An apparatus for distributing the load caused by the insertion of a fastening device into bony tissue is disclosed. In one embodiment, the apparatus comprises a crown having a plurality of protrusions. The protrusions may have any desired physical properties, and function to obtain purchase in the bony tissue. Preferably, the crown includes an opening that is selectively engageable with a spherical head of the fastening device. The opening preferably comprises a spherical curvature that allows the surfaces of the spherical head and the opening to maintain flush contact, even when the fastening device is inserted into the bony tissue at a non-orthogonal angle. When the fastening device is inserted into the bony tissue, the crown distributes the load over a wider section of the bone, allowing the bone to maintain its structural integrity.

9 Claims, 8 Drawing Sheets

LOAD DISTRIBUTION CROWN

FIELD OF THE INVENTION

The present invention relates to fastening devices used with bony tissue. More specifically, the present invention relates to an apparatus that distributes the load of a fastening device in order to prevent the structural integrity of the bony tissue from being compromised.

BACKGROUND OF THE INVENTION

The field of medical engineering is rapidly expanding due to advances in engineering, material science, and advances in the field of medicine. These advances have allowed doctors and engineers to work together to create instruments and devices that allow more accurate and effective diagnosis and treatment of a wide variety of ailments. The diagnoses and treatments enable patients to recover from injuries or diseases that used to be crippling, or even fatal.

One area of the human body that is of particular importance is the skeletal system. Advances in medical engineering and medicine have allowed doctors to treat a wide variety of ailments involving the skeletal system, including back, neck, and joint pain. In addition, advancements have allowed faster healing of breaks and fractures of bones. Of particular importance are breaks or fractures of the spinal cord, because they can result in severe pain or even paralysis.

One common method of fixing broken or fractured bones is through the use of a fixation device. Typically, this involves a screw or a nail being inserted into the bone. Often, the screw or nail functions to anchor other components of a medical device to the bone. Additionally, a fastener and fixation device may be used to join two parts of a bone, or to hold two bones together. For example, bone screws may be used in a spinal fixation system to immobilize two or more vertebrae. These fixation devices can be used in conjunction with other devices or components, such as plates that hold the bones together and prevent movement.

Despite the advances in medical engineering, fixation and other devices are susceptible to the inherent weaknesses of bones and other bony tissue. Further complicating the matter, bones may become weak, brittle, or lose strength for a number of reasons. For example, the patient's age and nutrition may be factors for bone strength. Additionally, the strength of the bones may vary based on the degree of damage to the bone from disease, trauma, or the like. As the structure or strength of a bone lessens, it becomes increasingly difficult to use it for placement of a fastener. Thus, a bony anatomy capable of receiving and securely holding a fastener when healthy may not be sufficiently strong enough to resist pressure from a screw head when in a weakened state. Because a fixation device requires penetration of the bone, the strength of the bone has to be considered. The insertion of fixation devices, such as screws, often requires the drilling of holes into the bone. As the head of the fastener contacts the bony anatomy, it can impart a localized concentration of stress or pressure that a weakened bone may not be able to withstand. The exertion of a significant load on a small area of the bone may cause it to chip, crack, fracture, collapse, or break.

When fixation devices are used in spinal applications, the movement of the vertebrae must also be taken into consideration. A significant problem with screws that are inserted into vertebrae is that they tend to "backout," or unscrew due to the motion of the bones. When a screw backs out, it can require additional invasive procedures in order to correct the problem. In addition, because vertebrae vary in shape and size, they are particularly susceptible to breaking or cracking.

A continuing need exists for a load distribution device that is able to accommodate screws at various angles of insertion. Furthermore, a need exists for a load distribution device that is able to prevent backing out of a fixation device and reduce the likelihood of undesired chipping, cracking, fracturing, or breaking of the bone when the fixation device is being inserted.

SUMMARY OF THE INVENTION

The present invention relates to a crown that distributes the load of a fastening device in order to reduce the chances of the structural integrity of the bone being undesirably compromised. The present invention may be used with any type of fastening devices, such as screws, nails, or the like that have any desired physical characteristics. The fastening device is preferably inserted through an opening in the load distribution crown. Preferably, both, the fastening device and the crown are configured and dimensioned to have complimentary interfaces. The complimentary interfaces allow the two surfaces to rest flush against one another. One advantage of allowing the two surfaces to be flush is that the load may be more evenly distributed over the bottom surface, or base, of the crown facing the bone in which the fastener is inserted. Another advantage of the complimentary interfaces is that the load may be distributed evenly even when the screw or fastener is inserted at a non-orthogonal angle.

In one embodiment, the bottom face of the crown lies substantially flush with the surface of the bone. In another embodiment, the crown is configured to have a slit or cut extending from its outer perimeter edge to the inner perimeter edge that defines the opening through which the fastener is inserted. The cut or opening may be further defined by two free ends of the crown. When a slit or cut is present, one end of the crown that defines the cut or slit may be disposed higher than the opposing end of the crown. As the fastener is inserted through the opening and into the bone, the head of the fastener may apply pressure to the surface of the crown and cause the crown to, flex or bend, thereby causing the free ends of the crown to move toward a common plane. In one embodiment, the free ends of the crown may move from about 0.1 mm to about 5 mm before reaching a common plane. In another embodiment, the free ends may move from about 0.5 mm to about 3 mm before reaching a common plane. The flexing of the material that forms the crown allows for the storage of potential energy in the crown that can be released if the screw backs out. In addition, the use of a slit or cut allows for gradual increasing and decreasing of load distribution by the crown as the fastener is inserted into or removed from the bone.

In one embodiment where a cut or slit is provided in the load distribution crown, the free ends of the crown may be configured to provide a tactile or audible signal to the physician about the degree to which the crown has flexed or deformed. Thus, in one embodiment of the invention, the free ends of the crown are configured to provide three or more audible signals to the physician. In one embodiment, at least one free end of the crown has at least one detent or protrusion that interferes with a portion of the opposing free end of the crown. As the free ends move toward a common plane, the detent or protrusion is capable of providing tactile or audible signal to the physician.

In one embodiment, the opposing free end of the crown has one or more detents configured such that moving the detent from the first free end of the crown past one or more detents of the opposing free end causes a tactile, or audible signal. In yet another embodiment, the opposing end may have one or more recesses or channels such that moving the detent from the first free end of the crown past one or more recesses or channels of the opposing end causes a tactile or audible signal. Some embodiments of the invention may combine one or more detents and recesses or channels on the same free end to provide a variety of signals. In one embodiment, the potential energy stored in the crown from its deflection is sufficient to overcome the interference caused by interferences between the free ends that provide signals to the physician. Thus, in some embodiments the crown is capable of at least partially moving back toward its initial configuration if a fastener is backed out or if pressure on the crown is relieved for any reason.

In yet another embodiment where the crown is configured to provide a plurality of tactile or audible signals, the pressure or force needed to create one signal is greater than the pressure or force needed to create another signal. For example, in one embodiment, the force or pressure needed to be applied by the fastener to the crown to move the free ends of the crown to create an initial signal is less than the force or pressure needed to be applied by the fastener to the crown to move the free ends of the crown to create a second signal.

In yet another embodiment where the crown is configured to provide a plurality of tactile or audible signals, the intensity of one signal is greater than the intensity of another signal. For example, if the signal provided is an audible "click" the signals may progressively increase in intensity to notify the physician of the degree of compression of the crown between the fastener head and the bone. Thus, in one embodiment, a final signal during compression may have the greatest intensity so that a physician is notified that further deployment of the fastener may risk damage to the bone or loss of purchase of the fastener in the bone.

To further promote bone contact over a substantially portion of the bottom surface of the crown, the crown may have protrusions that allow it to achieve contact or purchase with the bone even when the bony surface contacting the crown is uneven or has a depression in it, or even when the crown with a cut or slit has not deflected sufficiently for the bottom surface to fully contact the bone. One or more protrusions disposed over a location of the bony anatomy that is sunken or lower than other portions of the bone may be used to contact these lower portions of the surface.

One advantage of using protrusions is that the screw or fastener may be more likely to stay in place when used in combination with a crown. In addition, the protrusions may help minimize shearing or grinding of the bone during insertion of the screw. In one embodiment of the invention, a portion of the crown and screw have complimentary interfacing surfaces that permit the fastener to rotate or swivel relative to the crown. This allows the bottom surface of the crown to achieve contact with the bone even if the fastener is inserted of angle from an orthogonal direction.

Additionally, the fastener and crown may be configured so that portions of the complimentary surfaces initially interfere with each other until a threshold force between them is achieved. As the screw or fastener is urged to move further into the bone, the interference area may cause the crown to be pressed into the bone. Eventually, these downward forces exceed the force needed to push the fastener head beyond the interference region and into a receptacle of the crown having a complimentary curved surface corresponding to the surface of the fastener head.

In one embodiment, the present invention comprises an apparatus for distributing a fastener head load over an increased surface of the bone. The apparatus comprises a crown comprising one or more protrusions and an opening having a generally spherical curvature. The crown may comprise any desired material. Also included is a fastener including a head that may initially interfere with the spherical curvature of the opening as described above. Alternatively, the opening of the crown that receives the fastener head may be wide enough for the complimentary sliding surfaces to contact each other without passing through an interference area. The fastener is selectively engageable with the opening to allow the crown to distribute the load caused by the insertion of the fastener into bony tissue. In one embodiment, the radial loading caused by the torque required to insert the fastener is borne by the crown. The crown then transfers the radial loading to axial loading that is applied to the bone.

As noted above, the bottom surface of the crown that contacts bone may be configured with one or more protrusions, or alternatively may be substantially free of protrusions. When protrusions are used, it may be desirable to alter the length, concentration, and distribution of the protrusions depending upon the type of bone that the crown will contact. In one embodiment, the length of the protrusions is preferably between about 0.7 and about 1.2 mm. The concentration of the protrusions, which can be measured by the average peak-to-peak distance between the one or more protrusions, is between about 0.7 mm to about 1.0 mm. Another way to measure the concentration of the protrusions is by the average base to base distance between neighboring protrusions, which may be between about 0.5 and 1.0 mm. Thus, the protrusions may be sufficiently separated to provide flat surfaces on the bottom surface. Alternatively, the protrusions may form a sawtooth pattern.

Additionally, the shape of the protrusions may be configured and adapted for a particular application. In one embodiment, the protrusions comprise an angle. In such an embodiment, the angle from a base of the protrusion to a peak of the protrusion may be between about 55 degrees and about 65 degrees.

In some embodiments, the spherical curvature of the complimentary surface of the crown is configured and dimensioned to evenly distribute the load caused by the insertion of the fastener into the bony tissue at a non-orthogonal angle. In one embodiment, the tangents to the spherical curvature of the opening intersect. Depending on the size of the curved surface of the fastener head, this crown configuration may result in interference between the spherical head and the spherical curvature of the opening.

In another embodiment, the complementary surfaces of the crown and fastener head may be configured with a plurality of ridges, steps, or ledges extending substantially in a direction orthogonal to the rotational direction of the fastener. As the ridged surfaces of the fastener and crown begin to engage, and ultimately reach their final position, the ridges may help resist forces from micromotion or vibration that might cause the fastener to back out of its position.

In order to effectively distribute the load caused by the fastener, the total surface area of the base of the crown may be about 10 square mm or greater. In some embodiments, it may be desirable to deform the surface area of the base in order to match the contour of the base to the contour of the bone involved. In such embodiments, the force necessary to deform the crown is preferably substantially greater than the force necessary to insert the screw into the bony tissue. For instance, the force needed to bend or deform the crown may be about 5 times or greater than forces that may be imparted on the crown by the fastener during insertion into bone. This prevents the crown from being deformed during the insertion of the screw. In some embodiments, an incision, cut, or slot may be formed in either the top or base to aid in deforming the crown at one or more predetermined locations.

It is desirable to prevent the fastener from passing completely through the crown. This may be achieved by making the diameter of the crown opening, through which a threaded portion of a screw or body portion of a fastener may pass, at least between about 5% and 10% smaller than the diameter of the head of the fastener. To permit rotation or swiveling of the fastener relative to the crown, the diameter of the fastener may be from about 5% to about 30% less than the diameter of the diameter of the crown opening.

In another embodiment, the present invention comprises an apparatus for distributing a load in bony tissue. The apparatus comprises a fastener and a crown comprising an opening. The fastener is selectively engageable with the opening to allow the crown to distribute the load caused by the insertion of the fastener into bony tissue. In this embodiment, the crown may include at least one protrusion. In other embodiments, the number of protrusions may be about 30 or less. Furthermore, the length of the protrusions may be from about 0.1 mm to about 4 mm from tip or peak to base. The concentration of the protrusions may be measured by the average peak-to-peak distance between the one or more protrusions, which may be between about 0.4 mm to about 2.5 mm. Alternatively, the average base to base distance between neighboring protrusions may be between about 0.1 mm and about 1.5 mm. Some of the protrusions may comprise an angle wherein the angle from a base of the protrusion to a peak of the protrusion is between about 50 degrees and about 70 degrees.

In another embodiment, the present invention comprises an apparatus for distributing a load in a spinal fixation system. The apparatus comprises a fastener and a crown including a plurality of protrusions and an opening. The opening is configured and dimensioned to distribute the load caused by insertion of the fastener into bony tissue.

DETAILED DESCRIPTION OF THE PREFERRED EMBODIMENTS

Figure 1:
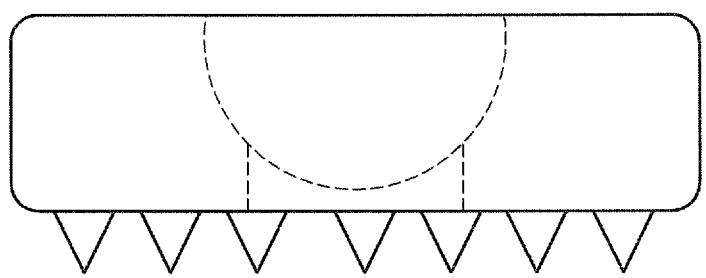
FIG. 1 is a diagram showing a side view of the crown according to an exemplary embodiment of the present invention.

Fastening devices are currently used in a wide variety of applications that range from construction to medical equipment. Typical fastening devices include nails and screws. Screws are often used as fastening devices in medical applications, typically to fasten a device to bony tissue or to provide temporary or permanent support.

In medical applications, one consideration when using a screw is the amount of force that the screw will exert on the bony tissue that it is inserted into. If a screw exerts too much pressure on bony tissue, it can compromise the structural integrity of the bone, which can cause many complications. The angle of insertion can also compromise the structural integrity of the bone. In some instances if the angle of insertion diverges significantly from a direction orthogonal to the bone it may cause the bone to crack or break. Thus, the angle of insertion and the pressure that a screw exerts are factors to consider when used in medical applications.

The present invention relates to a crown that that distributes the load of a fastening device in order to reduce the chances of the structural integrity of the bone being compromised. The present invention may be used with any type of fastening devices, such as screws, that have any desired physical characteristics. The fastening device is preferably inserted through the crown. Preferably, both the fastening device and the crown are configured and dimensioned to have complimentary interfaces. For instance, the complimentary surfaces may both have spherical curvatures and the radius of curvature for each surface may be substantially the same as the other such that contact between these surfaces is over an area instead of a point or line. Thus, it is preferred that the complimentary interfaces allow the two surfaces to maintain flush contact with one another yet also permit a range or motion or angulation between them to account for variations in the angle at which a fastener is inserted into the bone. One advantage of allowing the two surfaces to be flush is that the load may be evenly distributed over the bottom surface of the crown. Another advantage of the complimentary interfaces is that the load may be distributed evenly even when the screw is inserted at an angle.

It is desired that the base of the crown lies flush with the surface of the bone. The crown may have protrusions that allow the crown to achieve purchase in the bone. One advantage of the protrusions is that the screw is more likely to stay in place when used in combination with the crown than only a threaded screw. Another advantage of the protrusions is that they minimize grinding of the bone during insertion of the screw. To further decrease the chance of the screw backing out, the portion of the crown and screw that interface with each other may include complimentary uneven surfaces. The complimentary uneven surfaces create interference, which has to be overcome in order for the screw to be removed.

In one embodiment, the present invention may be used with any type of bony tissue, in any part of the body. For example, the present invention may be used in the spine, in long bones, in the skull, or in other parts of the skeletal system. In some embodiments, the shape of the surface of the crown that contacts the bone may be configured and dimensioned to rest flush with the surface of the bone. Accordingly, the crown may be used with a bone having any shape, for example, flat, round, irregular, or the like. In a preferred embodiment, the present invention is used for applications involving the spine. In such embodiments, the crown and fastener may be used with other devices to form, for example, a spinal fixation system.

FIG. 1 is a diagram showing a side view of a crown 20 according to an exemplary embodiment of the present invention. As shown in FIG. 1, the crown may have a plurality of protrusions 22 selectively positioned at the base of the crown. The protrusions 22 are preferably located on the base of the crown, which rests against the surface of the bone. In such an embodiment, the protrusions 22 allow the crown to achieve purchase in the bone as well as potentially accounting for variations or depressions in the surface of the bone. The protrusions may be varied in any aspect, such as size, shape, distribution, and the like, as described in more detail below.

In one embodiment, the protrusions 22 may be configured and dimensioned in any desired manner. In one embodiment, for example, the length of the protrusions may be varied. It may be desirable to vary the length of the protrusions 22 in order to achieve a desired amount of purchase in the bone. Alternately, it may be preferable to vary the length of the protrusions 22 based on the size, shape, or type of bone that is involved. In other embodiments, it may be desirable to vary the length of the protrusions 22 based on the region of the spine that is involved. For example, protrusions 22 for treating the cervical region may be shorter in length than protrusions 22 for treating the lumbar region.

The length or height of the protrusions 22 may be described according to the distance from the base of the protrusion to the tip, peak, or portion of the protrusion 22 that is furthest from the base. Preferably, the length of the protrusions is between about 0.1 and about 4 mm. More preferably, the length of the protrusions is between about 0.5 and about 2 mm, and most preferably the length of the protrusions is between about 0.7 and about 1.2 mm.

In one embodiment, a desired amount of purchase may be achieved by varying the number of protrusions 22 that are present. Generally, more protrusions 22 may yield better gripping of the bone under certain conditions, such as when the bony surface is relatively flat. However, if there are too many protrusions 22, the structural integrity of the bone may be compromised when they are driven into the bone. Plus, the force needed to drive the protrusions 22 into the bone may increase significantly. Furthermore, an abundance of protrusions may make the crown less capable of engaging with or contacting bony regions that are depressed or lower than other portions of the surface. Thus, it is desirable to choose the number, concentration, and distribution of protrusions 22 such that a sufficient purchase in the bone may be achieved without compromising the structural integrity of the bone. Preferably, the number of protrusions is about 40 or less. More preferably, the number of protrusions is about 20 or less, and most preferably the number of protrusions is about 10 or less.

Figure 2A:
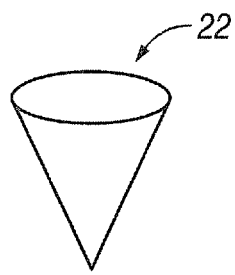
FIGS. 2A-2C are diagrams showing exemplary protrusions according to the present invention.
Figure 2B:
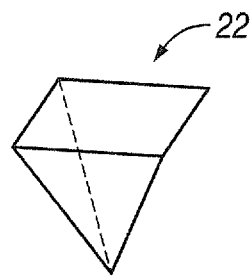
Figure 2C:
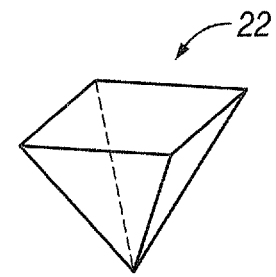

Another way to achieve a desired amount of purchase in the bone is to vary the geometric shape of the protrusions 22. FIGS. 2A-2C are diagrams showing exemplary protrusions according to the present invention. In some embodiments, it may be desirable to use conically shaped protrusions, as shown in FIG. 2A. Alternately, pyramid shaped protrusions, shown in FIG. 2B may be desired. The shape of the protrusions shown in FIGS. 2A-2B may be preferred when it is desirable for the crown to avoid motion once the screw has been completely driven into the bone or where the bony surface may be uneven. In other words, once the screw has been driven into the bone, the protrusions may at least partially pierce and extend into the bony surface.

In another embodiment, it may be preferable for each protrusion 22 to achieve a maximum amount of purchase in the bone by providing protrusions that more readily permits sliding in one direction while more substantially resisting motion in a second direction. Thus, angled (FIG. 2C) or curved protrusions may be used, and a plurality of them may be oriented on the bottom surface of the crown to permit rotational sliding in one direction more readily than in another direction. One advantage of an angled or curved protrusion is that it can be driven into the bone by applying a given amount of torque. Another advantage of an angled or curved protrusion is that it may be configured and dimensioned such that it provides more resistance to motion in one direction than in the other direction. Thus, when used in combination with complimentary interfering surfaces or textured surfaces, both of which are discussed in more detail below, the angled or curved protrusions may help prevent a fastener or screw from inadvertently coming loose or backing out.

As mentioned above, in some embodiments protrusions may comprise one or more angled edges. One way to describe these edges is by the angle from the point to the base of the protrusion 22. In some embodiments, the overall configuration, distribution, and number of protrusions may vary depending on the intended location in the spine where the crown may be inserted. For instance, some or all of the protrusions may have a sawtooth configuration having substantially symmetrical surfaces and angles off of a vertical axis that extends through the peak of the protrusion. Alternatively, as described above, the protrusions may have different angles off of the vertical axis so that the protrusions are more resistant to movement in one direction than in the opposite direction. In either case, the angle at which the side or sides of a protrusion extend from the peak to a base may form an angle of about 50° to about 70°, and preferably is about 60°.

Figure 3A:
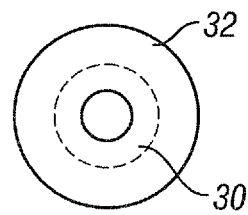
FIGS. 3A-3C are diagrams showing exemplary distributions of the protrusions.
Figure 3B:
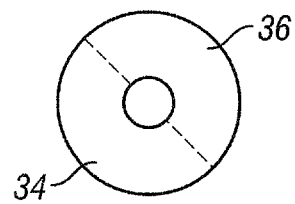
Figure 3C:
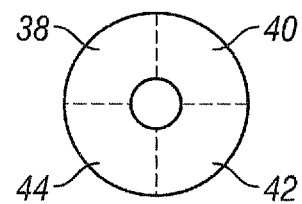

In addition to the length and geometric shape of the protrusions 22, the distribution of the protrusions around the base of the crown may be varied. FIGS. 3A-3C are views of the bottom surfaces of crowns, which ultimately will be pressed against the surface of the bone to distribute loading by the fastener over a greater area than the fastener head. The different views illustrate some of the different, non-limiting distributions or protrusions that may be used.

In one embodiment, the distribution of the protrusions may be varied according to the radial distance from the center of the crown. For example, the distribution of the protrusions may be varied over two regions 30-32, as shown in FIG. 3A. For example, protrusions in the outer circumferential region may be longer than the protrusions in the inner region. For instance, the average length of the protrusions in the outer region may be from about 5% to about 30% longer than the average length of protrusions in the inner region. In this manner, it is believed that the bony surface beneath this outer region will be more likely to be partially supporting the loading of the fastener. It should be understood that more than two regions of protrusions may be used as well. Alternatively, the distribution may be varied on each half 34-36 of the crown, as shown in FIG. 3B. In other embodiments, there may be a different distribution in each of several portions 38, 40, 42, and 44 of the crown, shown in FIG. 3C.

In some embodiments, such as the ones shown in FIGS. 3A-3C, the physical characteristics of the protrusions, such as length, shape, and the like, may be different in each region. In some embodiments it may be desirable to have different sized or shaped protrusions in each region. For instance, it may be preferable to have the protrusions in outer region 32 that are, for example, larger, longer, or sharper than the protrusions located in inner region 30. The protrusions in outer region 32 may be different than the ones located in the inner region 30 so to ensure that region 32 achieves sufficient purchase in the bone.

In one embodiment, the distribution of the protrusions 22 may be varied based on the type of bone that is involved. In these embodiments, it is desirable to vary the concentration of the protrusions. In other words, the number of protrusions for a given area may be increased or decreased, based on the type or shape of bone involved. For instance, when used in applications involving the lumbar region of the spine, a greater concentration of protrusions 22 may be desired. In contrast, a crown used in the cervical regions of the spine may have a lower concentration of protrusions. Not only may the protrusions 22 for the cervical region be less concentrated, but they also may be smaller in height that the protrusions that might be used for the lumbar regions.

One benefit a lower concentration of protrusions 22 can provide for treating a cervical region is that there is greater likelihood that the protrusions will fully or at least substantially extend into and grip the treated area in order to resist movement. In these embodiments, the portions of the crown where the protrusions 22 are located may not rest against the bone. This can occur when, for example, the bone is irregularly shaped or if it is not substantially flat. In contrast, when the spacer is in the lumbar region it may be more beneficial to have a higher concentration of protrusions in order to account for variations in anatomy between different patients. In general, the anatomy of vertebral bodies in the lumbar region may be curved, but the curvature of a vertebral body from one patient to another may vary. By having the protrusions densely packed together, any potential adverse effect on properly positioning the crown that may result from these differences in curvature can be minimized.

One way to describe the concentration of protrusions 22 on the crown may be by the average distance between the peak of a first protrusion to a neighboring one. For instance, a crown used in an application for treating the lumbar region of the spine may have an average peak-to-peak distance of about 0.4 mm to about 2.5 mm. In another embodiment, the average peak-to-peak value is from about 0.7 mm to about 1.0 mm. Similarly, one embodiment of a crown used in an application for treating the cervical region of the spine may have a peak-to-peak distance of about 0.3 mm to about 2.5 mm, while in another embodiment the distance may be from about 1.0 mm to about 1.5 mm. Preferably, the peak-to-peak distance is about 1.25 mm when the crown is intended to be used in applications that treat the cervical region of the spine.

Another way to describe the concentration of protrusions 22 on the base of the crown is by the average spacing between the bases of a first protrusion to a neighboring one. As protrusions 22 are spread farther apart, the surface of the crown in between the protrusions becomes larger. Thus, when a crown is used in applications for treating the cervical region of the spine, the average distance between the bases of the protrusions may be about from 0.1 mm to about 1.5 mm. In other embodiment, the average base-to-base distance between protrusions is from about 0.5 mm to about 1.0 mm. Preferably, the average base-to-base distance between neighboring protrusions is about 0.8 mm. As mentioned above, the protrusions 22 on a crown used in applications that treat the lumbar region of the spine may be located more closely to each other than the protrusions on a crown for other regions of the spine. For instance, the average distance between the bases of the protrusions may be from about 0 mm to about 1.0 mm. In another embodiment the average base-to-base distance is less than about 0.5 mm, and more preferably is less than about 0.25 mm.

In some embodiments, it may be desirable to determine the physical characteristics of the protrusions 22 based on their desired function. For example, in some embodiments it may be desirable to have the protrusions 22 partially pierce the bone to obtain a desired amount of purchase. The purchase that is achieved preferably prevents slippage and distributes the load as the screw is driven into the bone. When an excessive amount of force is exerted on the bone by the screw, the structural integrity of the bone may be compromised. One advantage of the protrusions 22 achieving partial purchase is that the load can be distributed prior to the screw being fully inserted into the bone. This preferably decreases the chance of the structural integrity of the bone being compromised by the force of inserting the screw. In addition, the partial purchase achieved by the protrusions 22 can provide stability for the screw. One advantage of the stability is that the crown is able to provide a guide for inserting the screw. This may be particularly important in applications where it is desirable to avoid interference between two or more inserted screws. These are just examples, and are not intended to limit the present invention. In other embodiments, the physical characteristics of the protrusions 22 can be chosen to perform a plurality of other functions, such as providing visual cues to a surgeon indicating that the screw is fully inserted.

Turning now to FIGS. 4A-4D, the physical characteristics of the crown are described. As mentioned above, one advantage of the present invention is that the load generated by the screw can be distributed over a larger surface area of bone such as over an area of at least about twice the area of the fastener screw head that would otherwise contact the bone. This prevents the structural integrity of the bone from being compromised from cracking, breaking, chipping, and the like. It is highly desirable to avoid these occurrences because it can result in a plurality of complications, such as longer healing time, longer or multiple surgeries, failure of the fastener to be securely held in position, and the like.

The load caused by the screw may be more widely distributed by increasing the overall area of the base of the crown. By increasing the area of the base, a larger portion of the crown may come into contact with the bone, thereby distributing the load over a larger area than would be expected from the fastener or screw head alone. However, practical applications require the size of the crown to be limited in order to, for example, fit within the body, be suitable for use with other devices, limit the profile of the combined screw and crown, and be used with bones of varying size and shape.

When considering the area over which the load of the screw may be distributed, only the surface area of the base of the crown should be considered. In some embodiments, the surface area of the base of the crown may be different than the surface area of the top of the crown. However, the load is only distributed over a surface area of the crown that is in contact with the surface of the bone. One way to describe the surface area of the base of the crown is by the total area that is capable of contact with a surface, such as a bone. Preferably, the total surface area of the base of the crown is about 10 $mm^2$ or greater. More preferably, the total surface area of the base of the crown is about 20 $mm^2$ or greater, and most preferably the total surface area of the base of the crown is about 30 $mm^2$ or greater.

In one embodiment, the shape of the crown may comprise any desired geometry. In some embodiments, as mentioned above, the shape of the top position of the crown and the shape of the base of the crown may be different. In these embodiments, it may be desirable to determine the shape of the bottom portion of the crown based on the desired surface area that is in contact with the surface of the bone. The geometry of the top of the crown is discussed in greater detail below.

However, in some embodiments, it may be desirable to have the geometry of the top and bottom surfaces substantially similar.

Figure 4A:
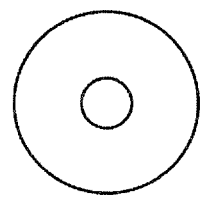
FIGS. 4A-4F are diagrams showing exemplary geometric configurations of the crown.

In one embodiment, the desired surface area of the base of the crown may be achieved using a plurality of shapes. In a preferred embodiment, a circular crown including a circular opening may be used, as shown in FIG. 4A. One advantage of a circular crown including a circular opening is that they are easy to manufacture. In addition, a substantially circular crown is believed to provide greater surface area coverage in a more compact configuration than may be achieved from other shapes.

Another advantage of the circular crown is that the screw, whose shaft is typically substantially circular, can easily fit through the circular opening. In some embodiments, the inner surface 48 may comprise threads that correspond to threads located on the surface of the shaft of the screw. In these embodiments, it is preferable to have a circular screw having a circular opening in order to correspond to the shape of the shaft of the screw.

Figure 4B:
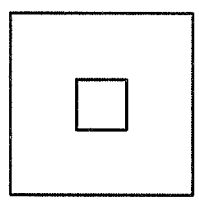
Figure 4C:
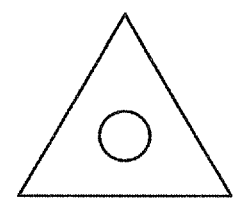
Figure 4D:
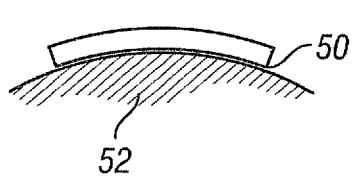
Figure 4E:
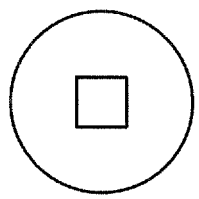
Figure 4F:

However, the base of the crown is not limited to any particular shape. In some embodiments, it may be desirable to have a square shaped base with a square opening, as shown in FIG. 4B. In other embodiments, it may be desirable to have the base of the crown comprise a triangular shape having a triangular opening, as shown in FIG. 4C. In the FIGS. 4B and 4C embodiments, the size of the opening is preferably configured and adapted such that it is able to pass the screw with a substantially small amount of resistance. In another embodiment, the shape of the base of the crown may be configured according to the expected neighboring surface of the bone. For example, as shown in FIG. 4D, at least the bottom portion of the crown 50 may have a generally cylindrical curvature when viewed from a side or otherwise may be configured according to the shape of the bone 52. In such embodiments the geometry of the top portion of the crown does not have to be substantially similar to the bottom portion of the crown. However, this may be desirable in some applications. In other embodiments, the shape of the outer perimeter of the base of the crown may be substantially different than the shape of the opening, as shown in FIGS. 4C and 4E. FIG 4F also illustrates a crown having a top portion that is of a different shape from the bottom portion of the crown.

In some applications, it may be desirable to allow a surgeon to change the geometry of some or all portions of the crown based on the shape of the bone. This provides the advantage of allowing a surgeon to visually inspect the bone and configure the shape of the crown accordingly. As discussed above, this may be desirable in order to further increase the contact between the base of the crown and the surface of the bone. This is because the load can only be distributed over the areas of the crown that are in contact with the surface of the bone. An uneven contact with the bone may cause the load to be increased over the areas of the crown that are in contact with the bone. This is undesirable for many reasons, for example, because it does not allow the crown to distribute the load in a predictable manner. This may have many detrimental effects including, but not limited to, cracking, chipping, or breaking of the surface of the bone.

In one embodiment, the crown may be designed such that it is capable of being deformed by a predetermined amount. In this embodiment, a surgeon would be able to visually inspect the surface of the bone and then deform the crown by a desired amount in order to conform to the surface of the bone, as illustrated in FIG. 4D. In one embodiment, the crown may comprise a material that is malleable using a given amount of force. This preferably occurs before the crown is placed in contact with the surface of the bone. However, it is undesirable to allow the crown to be deformed by, for example, the insertion forces of the screw. In one embodiment, the force required to deform the crown is greater than the insertion forces of the screw. This allows the crown to be deformed by a surgeon prior to placement in contact with the surface of the bone, but to maintain its shape subsequently. The desired deformation may be achieved using in any desired manner. For example, in one embodiment the deformation may be achieved using a machine or instrument that is capable of generating the required amount of force to deform the crown.

Figure 5A:
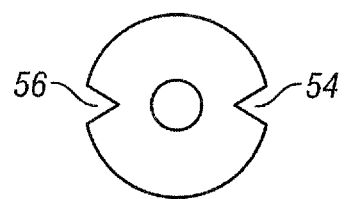
FIGS. 5A-5D are diagrams showing incisions according to an exemplary embodiment of the present invention.

In another embodiment, the crown may be deformable based on one or more incisions, or slits, that are formed in the base of the crown. FIG. 5A is a diagram showing a bottom view of an exemplary base of the crown. In this embodiment, two or more diagonal slits 54-56 are formed in the base of the crown. The slits 54-56 are preferably formed from the opening to the outer perimeter of the base of the crown. The slits may allow the crown to have greater flexibility and bending while still distributing loading over a larger area than the fastener or screw head. Some flexibility of the crown may permit it to better engage with an uneven bone surface, which may allow the base of the crown to achieve maximum contact with the surface of the bone.

Figure 5B:
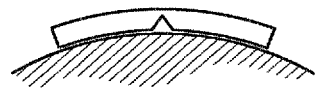
Figure 5C:
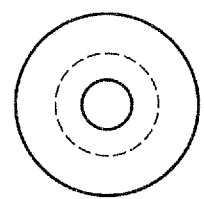

In the FIG. 5A embodiment, two diagonal slits 54-56 are formed. However, more than two slits may be used, as desired according to a particular application, and they need not all be oriented in a generally radial direction as shown in FIG. 5A. For example, one or more notches on the bottom or top surface of the crown may allow the crown to be flexed or bent to conform to the shape of the bone, as shown in FIG. 5B. In other embodiments, it may be desirable to have slits formed in other directions. For instance, in one embodiment, it may be desirable to have one or more circumferential slits formed in the base or on the top surface of the crown. The radial slit is preferably formed at a predetermined distance between the opening and the outer perimeter of the base of the crown, such as in a central region between about 25% to about 75% of the distance from the center of the crown to its outer peripheral edge. One advantage of a circumferential slit is that it allows the crown to be deformed at selected areas around the perimeter of the crown, while allowing other portions to maintain their given shape or contour. This may be particularly useful in applications involving irregularly shaped bones, such as those in the cervical spine.

Figure 5D:

In other embodiments, it may be desirable to have the slits formed near the interface between the fastener and the crown, as shown in FIG. 5D. In the FIG. 5D embodiment, two or more diagonal slits are formed from the opening to the outer perimeter of the top of the crown. As shown in the FIG. 5D diagram, the slits allow the crown to be deformed according to the contour of the bone. In other embodiments, radial slits may be configured and dimensioned near the interface between the fastener and the crown. In each of the FIG. 5A-5D embodiments, the slits allow sufficient deformation to match the contour of the surface of the bone. However, it is desired that the crown is sufficiently rigid to resist the insertion forces of the fastener.

Figure 6A:
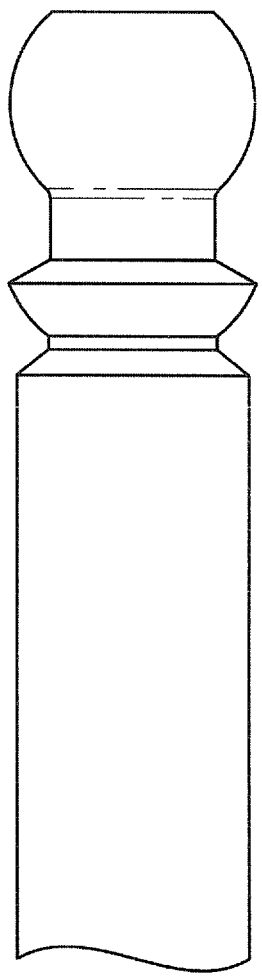
FIG. 6 is a diagram showing a screw according to an exemplary embodiment of the present invention.
Figure 6B:
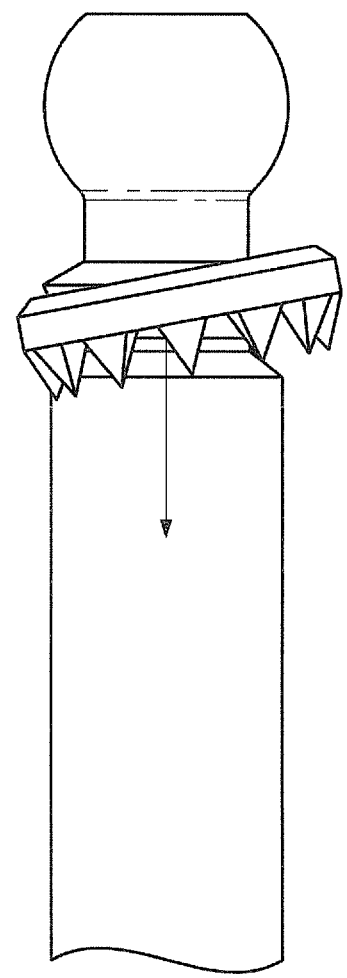

In one embodiment, the present invention is used to distribute the load generated by inserting a fastener into bony tissue. As discussed above, the fastener may be a screw. Any type of screw may be used, depending on a particular application. FIGS. 6A and 6B are illustrations of one embodiment of a fastener or screw that may be used with a crown according to the present invention. The fastener or screw preferably has a spherical head 58 that is selectively engageable with a spherical curvature 46 of the crown, discussed in more detail below. An elongate shaft 60 is connected to the spherical head 58 to allow it to penetrate bony tissue of the vertebrae. Preferably, the elongate shaft 60 includes threads that aid in inserting the screw into bony tissue and holding it in place. In some embodiments, the screw may include a projection, for example, a hexagonal projection, to aid in gripping the screw.

The top portion of the crown is preferably configured and adapted to receive the screw. In some embodiments, it is desirable to insert the screw into the bone at an angle, that is not perpendicular to the surface of the bone. In such embodiments, it is still desirable for the load to be distributed evenly by the crown. In order to evenly distribute the load, it is desirable for the base of the crown to remain in contact with the surface of the bone regardless of the angle of insertion of the screw. One way to do this is through the use of a partial ball and socket interaction. In other words, the surface of the crown around the opening may be configured to have a spherical curvature. The spherical curvature preferably allows the interface between the spherical head 58 of the screw and the crown to be flush for a variety of angles of insertion.

Figure 7A:
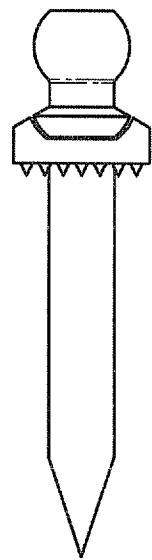
FIGS. 7A-7C are diagrams illustrating the spherical curvature of the opening of the crown.
Figure 7B:
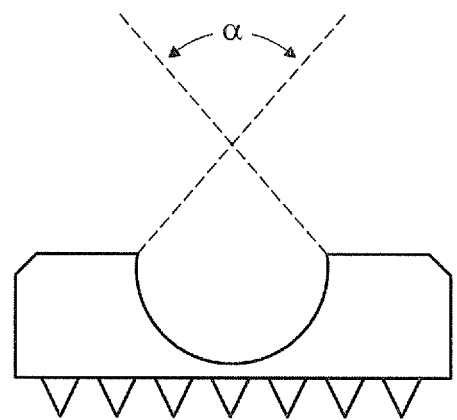

FIG. 7A is a diagram showing a side view of an exemplary crown. In this embodiment, the opening comprises a surface having a spherical curvature. The spherical head of the screw preferably interacts with the spherical curvature of the crown, in order to provide flush contact between the two surfaces. In one embodiment, tangents to the spherical curvature of the opening diverge above the upper surface of the crown, as shown in FIG. 7B. This allows the spherical head 58 of the screw to remain flush with the spherical curvature of the opening even at large angles of insertion.

Figure 7C:
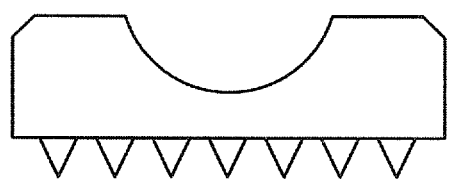

In some embodiments, tangents to the curvature of opposing points along the spherical curvature of the crown may intersect at a location above the upper surface of the crown, as shown in FIG. 7C. One advantage of having the tangents to the curvature intersect is that the spherical curvature of the opening generates an interference area. As the head 58 of the screw is being screwed into place, a sufficient amount of force may be applied to force the head 58 of the screw to contract slightly. As the screw continues into the bone, the head 58 of the screw is able to pass through the interference area. Once the head 58 of the screw passes through the interference area it fits into the spherical curvature of the opening. It is desirable that forces that cause the screw to backout are not strong enough to force the screw back through the interference area. The resistance of the interference area may be modified by changing increasing or decreasing its curvature.

Returning to FIG. 7C, the tangents to the spherical curvature may intersect to form an angle. This angle is preferably between about 0.1 and about 20 degrees, or alternatively may be from about 0.5 to about 10 degrees. In another embodiment, the angle between the tangents is between about 1 and about 5 degrees, while in yet another embodiment the angle may be between about 1 and about 3 degrees.

Another advantage of the spherical curvature shown in FIGS. 7A-C is that a screw may be inserted into bony tissue at any desired angle. In other words, the screw does not have to be inserted perpendicular to the crown. The interference area, caused by the spherical properties of the head 58 of the screw and the spherical curvature of the opening, are preferably sufficient to prevent the screw from backing out. While opening prevents the screw from backing out, it allows it to rotate freely. One advantage of allowing the screw to rotate freely is that the crown according to the present invention is able to accommodate movements of bone, for example, cervical vertebrae. Another advantage of allowing the screws to be inserted at any angle is that it allows relatively close spacing of the screws, without the risk of interference with one another.

In order to allow the screw to be inserted at any desired angle, the opening is preferably large enough to allow for a wide range of motion. As described above with respect to FIGS. 4A-4E, the opening may comprise a variety of shapes. Regardless of the shape of the opening, the total area formed by the opening is preferably large enough to accommodate the shaft 60 of the screw. However, the opening is preferably small enough that it does not permit the spherical head 58 of the screw to completely pass through the opening. Because of the varying shapes and sizes of the opening, it is convenient to describe the relationship between the spherical head 58 of the screw and the opening in terms of the diameter of the smallest part of the opening. In other words, the diameter of the smallest part of the opening should be sufficiently small to prevent the spherical head 58 from completely passing through the crown. This is desirable in some applications in order to allow a surgeon to remove the screw when desired. Preferably, the diameter of the smallest part of the opening is about 30% or less smaller than the spherical head 58 of the screw. More preferably, the diameter of the smallest part of the opening is about 15% or less smaller than the head 58 of the screw, and most preferably the diameter of the smallest part of the opening is about 5% or less smaller than the head 58 of the screw. The relationship between the spherical head 58 and the opening can also be expressed according to the size of the head 58 relative to the opening. Preferably, the diameter of the spherical head is between 5% and 40% larger than the diameter of the smallest portion of the opening. More preferably, the diameter of the spherical head is between about 10% and about 30% larger, and most preferably the diameter of the spherical head is between about 15% and 25% larger than the diameter of the smallest portion of the opening.

In many applications, it is desirable to prevent backout of the screw. One way to do this is by creating an interference area, as described above. In another embodiment, a plurality of ridges may be selectively positioned along the inner surfaces of the opening. In some embodiments, a complimentary set of ridges are selectively positioned along the surface of the spherical head 58 of the screw. One advantage of the ridges is that they create interference between the crown and the screw head such that the crown would also have to turn in order for the screw to back out, or to be unscrewed. This may be advantageous in applications involving, for example, the cervical spine. In these applications, screws are often used to connect a plate or other device to one or more vertebrae. Backing out of a screw often occurs in these applications because of the movement of the vertebrae. Thus, preventing backing out using ridges or an interference area is highly desirable.

It may also be desirable for the load distribution crown to gradually increase or decrease application of pressure on the bone as the fastener is deployed further into or out of the bone. One benefit of this feature is that the physician may have greater control over the degree of pressure applied to the bone from the fastener head. One way that these features may be provided in a load distribution crown is to configure the crown with a spring-like mechanism that, when compressed or turned, applies progressively greater forces against the bone until reaching maximum deflection. FIGS. 8A-D illustrate, several non-limiting examples of how a load distribution mechanism may be configured with a spring that deflects and applies a force to the surface of the bone as the fastener is inserted.

Figure 8A:
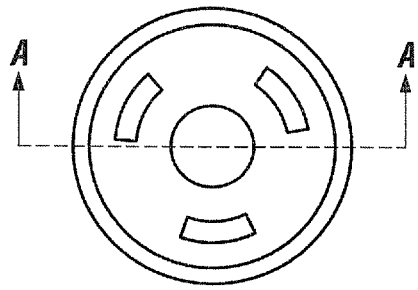
FIGS. 8A-8D are illustrations of embodiments of the present invention having a spring mechanism capable of deflecting to provide gradually increasing or decreasing pressure on the bone in response to fastener movement.
Figure 8B:
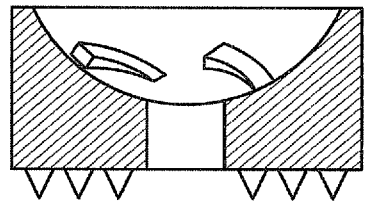

FIGS. 8A and 8B, for example, show that a portion of the upper surface of the crown that communicates with the fastener head may have one or more tabs or protrusions that can deflect under axial loading by the fastener. Thus, as the fastener is turned or otherwise moved further into the bone, the tabs or protrusions on the upper surface of the crown will bend or deflect under the loading until the fastener head is in full contact with the upper surface of the crown. The upper surface of the crown may have recesses formed therein corresponding to the shape of the one or more tabs or protrusions so that as the tabs or protrusions are deflected they can move into the recesses. In one embodiment, the fully deflected tabs or protrusions are substantially flush with the remaining surface of the crown in contact with the fastener head.

Furthermore, an edge of the tabs or protrusions may be configured to provide one or more tactile or audible signals to the physician to indicate the degree of deflection that has already occurred or that remains before full deflection. For example, an edge of one or more tabs or protrusions may have a detent that at least initially interferes with an edge of the recess. As the fastener is driven further into the bone, however, the forces applied on the tabs or protrusions eventually may cause the detent to move beyond the interference area, thereby indicating to the physician that further progress of the fastener into the bone may cause damage to the bone, cause the fastener to lose its purchase in the bone, or both.

Figure 8C:
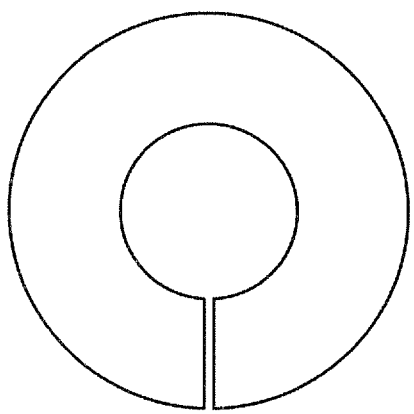
Figure 8D:
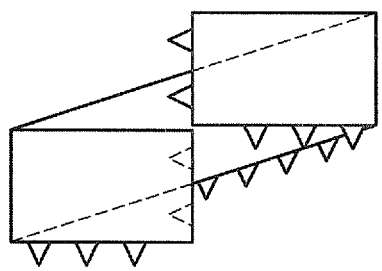
Figure 9:
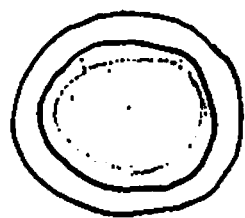
FIG. 9 is a top view of a fastener with a spherical head having a diameter between about 5% and 30% larger than a diameter of an opening in the head according to some embodiments.
Figure 10:
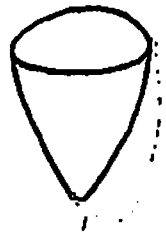
FIG. 10 is a front view of a curved protrusion according to some embodiments.
Figure 11:
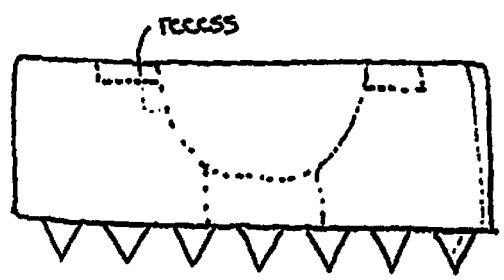
FIG. 11 is a front view of a crown body with a recess formed on an upper portion of the crown body.

In another embodiment, illustrated in FIGS. 8C and 8D, the crown is configured to have a slit or cut extending from its outer perimeter edge to the inner perimeter edge that defines the opening through which the fastener is inserted. The cut or opening may be further defined by two free ends of the crown. When a slit or cut is present, one end of the crown that defines the cut or slit may be disposed higher than the opposing end of the crown. As the fastener is inserted through the opening and into the bone, the head of the fastener may apply pressure to the surface of the crown and cause the crown to flex or bend, thereby causing the free ends of the crown to move toward a common plane. In one embodiment, the free ends of the crown may move from about 0.1 mm to about 5 mm before reaching a common plane. In another embodiment, the free ends may move from about 0.5 mm to about 3 mm before reaching a common plane. The flexing of the material that forms the crown allows for the storage of potential energy in the crown that can be released if the screw backs out. In addition, the use of a slit or cut allows for gradual increasing and decreasing of load distribution by the crown as the fastener is inserted into or removed from the bone.

In one embodiment where a cut or slit is provided in the load distribution crown, such as illustrated in FIG. 8D, the free ends of the crown may be configured to provide a tactile or audible signal to the physician about the degree to which the crown has flexed or deformed. Thus, in one embodiment of the invention, the free ends of the crown are configured to provide three or more audible signals to the physician. In one embodiment, at least one free end of the crown has at least one detent or protrusion that interferes with a portion of the opposing free end of the crown. As the free ends move toward a common plane or position, the detent or protrusion is capable of providing tactile or audible signal to the physician.

In one embodiment, the opposing free end of the crown has one or more detents configured such that moving the detent from the first free end of the crown past one or more detents of the opposing free end causes a tactile or audible signal. In yet another embodiment, the opposing end may have one or more recesses or channels such that moving the detent from the first free end of the crown past one or more recesses or channels of the opposing end causes a tactile or audible signal. Some embodiments of the invention may combine one or more detents and recesses or channels, on the same free end to provide a variety of signals. In one embodiment, the potential energy stored in the crown from its deflection is sufficient to overcome the interference caused by interferences between the free ends that provide signals to the physician. Thus, in some embodiments the crown is capable of at least partially moving back toward its initial configuration if a fastener is backed out or if pressure on the crown is relieved for any reason.

In yet another embodiment where the crown is configured to provide a plurality of tactile or audible signals, the pressure or force needed to create one signal is greater than the pressure or force needed to create another signal. For example, in one embodiment, the force or pressure needed to be applied by the fastener to the crown to move the free ends of the crown to create an initial signal is less than the force or pressure needed to be applied by the fastener to the crown to move the free ends of the crown to create a second signal.

In yet another embodiment where the crown is configured to provide a plurality of tactile or audible signals, the intensity of one signal is greater than the intensity of another signal. For example, if the signal provided is an audible "click" the signals may progressively increase in intensity to notify the physician of the degree of compression of the crown between the fastener head and the bone. Thus, in one embodiment, a final signal during compression may have the greatest intensity so that a physician is notified that further deployment of the fastener may risk damage to the bone or loss of purchase of the fastener in the bone.

Though the present invention has been described with respect to several embodiments, those skilled in the art will recognize that the invention is capable of alternate embodiments within the scope of the appended claims.

The invention claimed is:

1. An apparatus for distributing a load in a spinal fixation system, comprising:
    a fastener;
    a crown body including a plurality of protrusions and an opening extending longitudinally therethrough and a radial slit extending from the opening to an outer perimeter edge;
    wherein the opening is configured and dimensioned to distribute the load caused by insertion of the fastener into bony tissue, and
    wherein first and second free ends of the crown body are configured adjacent the radial slit and the first free end is disposed higher than the second free end
    wherein the first free end is configured with at least one protrusion that interferes with the second free end of the crown body so as the first free end moves toward a final position, the at least one protrusion is capable of providing tactile or audible signals.

2. The apparatus according to claim 1, wherein the number of protrusions is about 40 or less.

3. The apparatus according to claim 1, wherein the length of the protrusions is between about 0.1 and about 4 mm.

4. The apparatus according to claim 1, wherein the average peak-to-peak distance between the one or more protrusions is between about 0.4 mm to about 2.5 mm.

5. The apparatus according to claim 1, wherein the one or more of the plurality of protrusions include a base, wherein the average base to base distance between neighboring protrusions is between about 0.1 and 1.5 mm.

6. The apparatus according to claim 1, wherein the protrusions comprise an angle, wherein the angle from a base of the protrusion to a peak of the protrusion is between about 50 degrees and about 70 degrees.

7. The apparatus according to claim 1, wherein the total surface area of a base of the crown is about 10 square mm or greater.

8. The apparatus according to claim 1, wherein the crown is capable of being deformed by a predetermined amount.

9. The apparatus according to claim 8, wherein a force necessary to deform the crown is greater than the force necessary to insert the fastener into the bony tissue.

* * * * *